United States Patent [19]

Hawkins, Jr. et al.

[11] Patent Number: 4,790,812
[45] Date of Patent: Dec. 13, 1988

[54] APPARATUS AND METHOD FOR REMOVING A TARGET OBJECT FROM A BODY PASSSAGEWAY

[76] Inventors: Irvin F. Hawkins, Jr., c/o Mail Department, Radiology, Shands Teaching Hospital, University of Florida, Gainesville, Fla. 32601; Mark C. Hawkins, R.R. #2, Box 178, Micanopy, Fla. 32667

[21] Appl. No.: 798,563

[22] Filed: Nov. 15, 1985

[51] Int. Cl.$^4$ ............................................. A61B 17/20
[52] U.S. Cl. ......................................... 604/22; 604/27; 604/35; 604/43; 604/267; 128/305; 128/328
[58] Field of Search ........................ 604/22, 27, 35, 43, 604/53, 266, 267; 128/305, 305.1, 311, 318, 328, 348.1, 356, 751, 752, 755, 757, 758, 304, 303 R

[56] References Cited

U.S. PATENT DOCUMENTS

| | | |
|---|---|---|
| 3,128,768 | 4/1964 | Geistauts ........................... 128/305.1 |
| 3,320,957 | 5/1967 | Sokolik ................................ 128/311 |
| 3,565,062 | 2/1971 | Kurls .................................. 128/303 |
| 3,614,953 | 10/1971 | Moss ................................ 128/305.1 |
| 3,635,223 | 1/1972 | Klieman ............................. 128/356 |
| 3,730,185 | 5/1973 | Cook et al. ......................... 128/305 |
| 3,732,858 | 5/1973 | Banko ................................ 128/753 |
| 3,749,085 | 7/1973 | Wilson et al. ....................... 128/305 |
| 4,020,847 | 5/1977 | Clark, III ........................... 128/751 |
| 4,228,802 | 10/1980 | Trott ................................. 604/267 |
| 4,445,509 | 5/1984 | Auth .................................. 128/305 |
| 4,557,255 | 12/1985 | Goodman .......................... 128/328 |
| 4,589,412 | 5/1986 | Kensey ............................. 128/305.1 |
| 4,606,330 | 8/1986 | Bonnet .............................. 128/328 |
| 4,611,594 | 9/1986 | Grayhack et al. ................. 128/328 |
| 4,631,052 | 12/1986 | Kensey ............................. 128/305 |
| 4,679,557 | 7/1987 | Opie et al. ......................... 128/305 |
| 4,681,106 | 7/1987 | Kensey et al. .................... 128/305 |

FOREIGN PATENT DOCUMENTS

| | | | |
|---|---|---|---|
| 2821048 | 11/1979 | Fed. Rep. of Germany ...... 128/328 |
| 0764684 | 9/1980 | U.S.S.R. ............................ 128/325 |

OTHER PUBLICATIONS

Applicant's Supplemental Disclosure Statement—enclosed figures of presentation to American Roentgen Ray Society (Feb. or Apr. 1984).
L. J. Greenfield et al, *Hemodynamic and Respiratory Responses to Transvenous Pulmonary Embolectomy*, J. Thorac. Cardiovasc. Surg. 62:890-897 (1971).
L. J. Greenfield, et al., *Transvenous Management of Pulmonary Embolic Disease*, Ann. Surg., 180:461-468 (1974).
K. W. Sniderman, et al., *Percutaneous Embolectomy by Transcatheter Aspiration, Radiology*, 150:357-361 (1984).
T. Akimoto, *Coronary Artery Thrombus Extirpation Catheter,* Bulletin of the Heart Institute, Japan, pp. 49–58 (1969).

*Primary Examiner*—C. Fred Rosenbaum
*Assistant Examiner*—Mario Costantino
*Attorney, Agent, or Firm*—Finnegan, Henderson, Farabow, Garrett & Dunner

[57] ABSTRACT

An apparatus and method for removing a target object from a body passageway. The apparatus comprises a catheter, a spiral wound coil disposed within the catheter and rotatably driven by an air actuated drive means, and a parachute basket. The spiral wound coil has a cutting tip at its distal end which is housed within the distal tip of the catheter and is prevented from extending outside the catheter by a grommet. In most situations, the target object is fragmented by the cutting action of the tip of the spiral wound coil as it is rotated at high speed within the catheter by the air actuated drive means. Rotation of the spiral wound coil also facilitates transport of the target fragments through the catheter lumen simultaneously with aspiration. The parachute basket is deployed downstream of the target object in order to capture any target fragments not aspirated into the catheter lumen. In situations where it is necessary to fragment relatively hard objects, such as atheroma or kidney stones, a drilling tool rotatably driven by a second air actuated drive means may also be provided which can be advanced through the distal open end of the catheter.

15 Claims, 4 Drawing Sheets

APPARATUS AND METHOD FOR REMOVING A TARGET OBJECT FROM A BODY PASSSAGEWAY

BACKGROUND OF THE INVENTION

The present invention relates generally to the field of medical devices and, more particularly, to devices and methods for removing objects from within a body passageway, such as a blood vessel.

Cardiovascular disease, including coronary thrombosis, is the leading cause of death in the United States. It has been estimated that at least 280,000 cases of pulmonary emboli occur annually in the United States, with slightly less than 50% mortality. Streptokinase has gained popularity in the treatment of pulmonary embolism and thrombophlebitis, most recently being used for occluded grafts and thrombosis associated with atherosclerotic disease (coronary arteries and extremities). In these situations, prompt removal is critical, since a delay in restoration of flow results in irreparable tissue damage. Unfortunately, several hours of streptokinase infusion may be required to remove large clots. Thus, this procedure is too often ineffective.

Greenfield et al. have developed a method for percutaneous clot removal using a cup-like device attached to a steerable catheter. This method is disclosed in the following articles: L. J. Greenfield et al., *Transvenous Management of Pulmonary Embolic Disease*, Ann. Surg., 180:461-468 (1974); L. J. Greenfield et al., *Hemodynamic and Respiratory Responses to Transvenous Pulmonary Embolectomy*, J. Thorac. Cardiovasc. Surg., 62:890-897 (1971). As the clot is sucked into the cup, the catheter is retracted. In most cases, the disadvantageous size of the system and the possibility of dislodging the clot from the cup during retrieval make this method less than satisfactory.

The use of a non-tapered catheter inserted into a vessel through a sheath to remove thrombi from peripheral vessels by transcatheter aspiration is known, such being most recently described in the following article: K. W. Sniderman et al., *Percutaneous embolectomy by transcatheter aspiration*, Radiology, 150:357-361 (1984). Unfortunately, such catheters exhibit problems when the thrombus is too large to be aspirated within the catheter lumen, therefore requiring an active method of fragmentation and transport.

An active method of fragmentation and transport of a thrombus within a catheter tube is described in T. Akimoto, *Coronary Artery Thrombus Extirpation Catheter*, Bulletin of the Heart Institute, Japan, pages 49-58 (1969). The apparatus and method disclosed therein involved the use of a spiral wire rotatably driven within a polyethylene catheter tube. Rotation of the spiral wire within the tube facilitated transcatheter transportation of the thrombus by screw movement. A blunt ring on the tip of the spiral wire extended outside the catheter in order to destroy the thrombus. Unfortunately, this apparatus was abandoned since in dog coronary arteries the loop perforated the arteries frequently.

SUMMARY OF THE INVENTION

According to one embodiment of the present invention, an apparatus is disclosed for removing a target object from a body passageway. The apparatus comprises a catheter having proximal and distal open ends and defining a central lumen therethrough. The catheter is sized to be transluminally advanced within the body passageway. There is further provided a spiral wound coil rotatably disposed within the central lumen of the catheter. The spiral wound coil is resilient and flexible along its length and has a cutting tip disposed at the distal end of the coil. The central lumen of the catheter at the distal end has a narrowed opening defined by a grommet end which is sized to prevent the cutting tip of the coil from extending out the distal end of the catheter during use. In addition there is provided a first drive means for rotatably driving the spiral wound coil within the catheter central lumen.

In use, the catheter with the spiral wound coil disposed therein is advanced through the body passageway to the site of the target object. The target object is fragmented by the cutting action of the tip on the spiral wound coil as it is rotated at high speed within the catheter by the air actuated drive means. The cutting tip is maintained in its proper position relative to the distal end of the catheter by the spring bias of the spiral wound coil normally urging against the grommet. Rotation of the spiral wound coil also facilitates transport of the target fragments outside the body through the catheter lumen.

Accordingly, it is an object of the present invention to provide an improved apparatus and method for removing a target object from a body passageway.

It is a further object of the present invention to provide an improved apparatus and method for removing a target object from a body passageway which is particularly useful for removing blood clots quickly and efficiently in emergency situations.

Related objects and advantages of the present invention will become more apparent by reference to the following figures and detailed description.

DESCRIPTION OF THE PREFERRED EMBODIMENT

Figure 1:
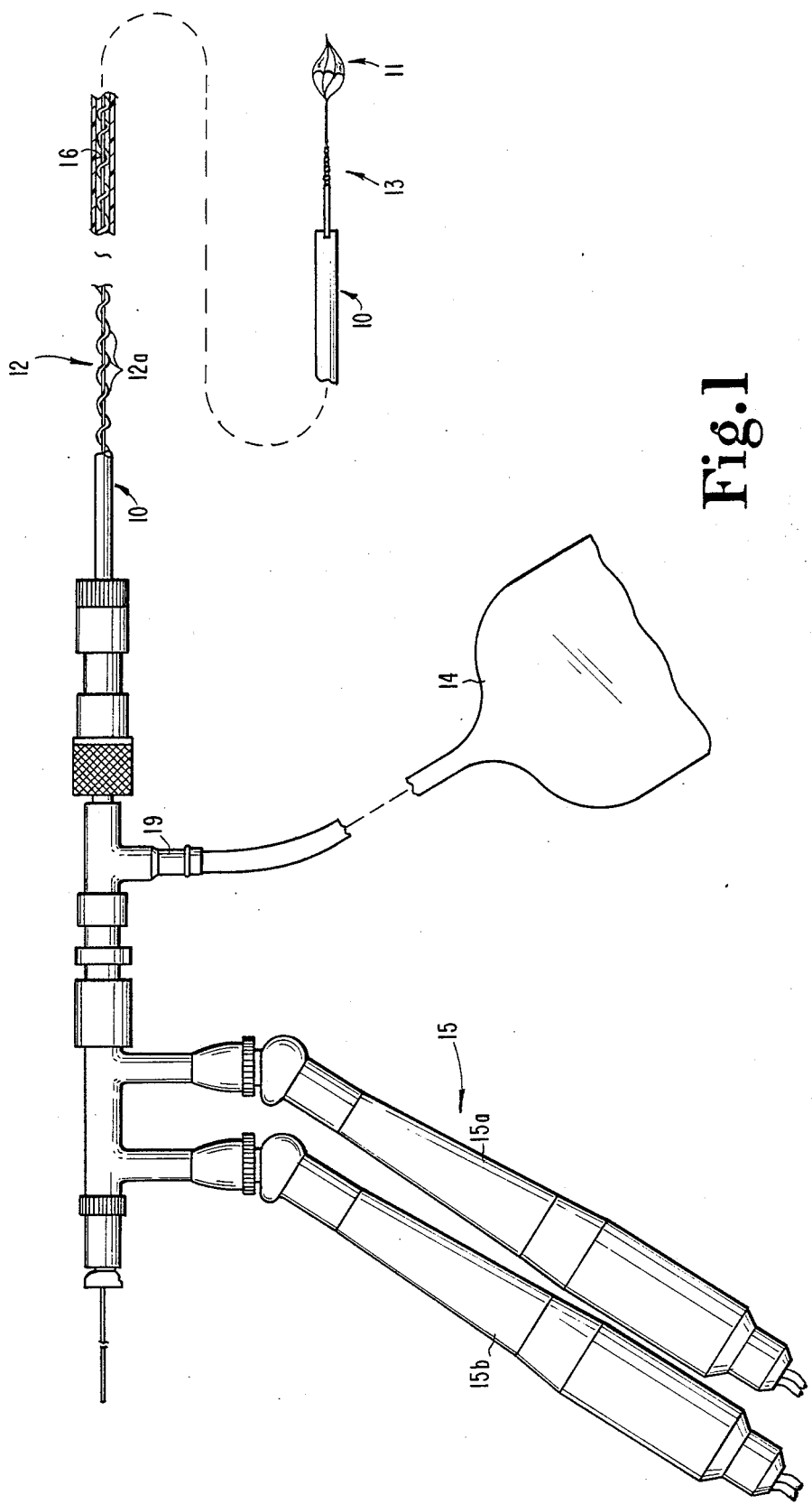
FIG. 1 is a framentary elevation view of the apparatus of the present invention with sections thereof broken away to show interior portions.
Figure 2:
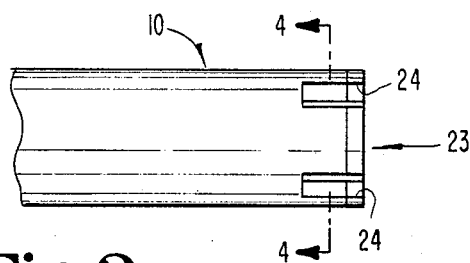
FIG. 2 is an enlarged fragmentary elevation view showing the distal end of the catheter of the present invention.
Figure 3:
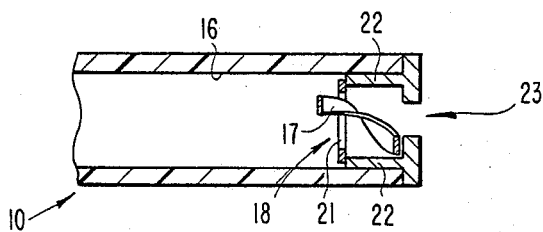
FIG. 3 is a full section view of the catheter of FIG. 2.
Figure 4:
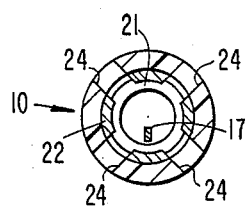
FIG. 4 is a section view taken along lines 4—4 in FIG. 2.

For the purposes of promoting an understanding of the prinicples of the invention, reference will now be made to the embodiment illustrated in the drawings and specific language will be used to described the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings in detail, there is depicted a preferred embodiment of the apparatus of the invention, which is useful for removing objects, particularly blood clots, gallstones and kidney stones, purulent material and atheroma, restricting the flow through a body passageway or cavity. The apparatus generally includes an elongate flexible catheter 10, a collapsible parachute basket 11, a spiral wound coil 12, a drilling device 13, a suction device 14, and a drive means 15 operable to rotatably drive the spiral wound coil 12 and drilling device 13 within the catheter 10.

Referring to FIGS. 1-4, the catheter 10 is generally tubular shaped and has a central lumen 16 in which is rotatably disposed the spiral wound coil 12. A side port 19 connects suction device 14 with lumen 16 of catheter 10, thus providing aspiration inside catheter 10. Suction device 14 may be of any type, such as a syringe or a vaccuum pump, which is conventionally known and otherwise suitable for this purpose. Spiral wound coil 12 comprises a series of loosely or tightly wound wire helices 12a which at the proximal end are fixedly coupled by a suitable quick release coupling (not shown) to the output shaft an air actuated motor 15a. At the distal end of the wire helices, the coil 12 terminates in part spiral cutting tip 17. The cutting tip 17 rotates within a metal grommet 18 press fit within the distal open end 23 of catheter 10. Coil 12 is preferably made of a spring flat wire steel construction. Alternatively, coil 12 may employ a round wire construction and may also be made of a molded flexible nylon or other polymer material.

The spiral wound coil 12 is longer in length than catheter 10 such that when the coil 12 is inserted in catheter 10 the helices are normally compressed and the distal most helix urges against ring shaped portion 21 of grommet 18. The ring shaped portion 21 of grommet 18 is sized to decrease the diameter of lumen 16 sufficiently to prevent the cutting tip of spiral wound coil 12 from extending outside the distal open end of catheter 10.

Grommet 18 includes a series of four angularly spaced apart wear resistant metal projections 22 which extend distally from ring shaped portion 21 to the distal open end 23 of catheter 10. The projections 22 and distal portion of catheter 10 together define a series of four angularly spaced apart and side opening slots 24 which communicate between lumen 16 and the exterior of catheter 10. Cutting action is provided by rotation of cutting tip 17 across the projections 22 in the space between positioning ring 21 and the distal open end 23 of catheter 10.

It should be understood that the size and length of catheter 10 and spiral wound coil 12 will vary according to the size and length of the passageway through which they are to be advanced in order to gain access to the target site. Further, catheter 10 may be formed from any material which is compatible for insertion within a body and which is sufficiently flexible to permit its advancement around curves or bends such as may typically be encountered. While FIG. 1 shows catheter 10 having only one lumen, it may be desirable in some situations to employ a bilumen catheter 20, such as is shown in cross section in FIG. 5, otherwise similar to catheter 10 but having a relatively smaller sized second lumen 30 for purposes such as allowing saline injection.

Figure 6:
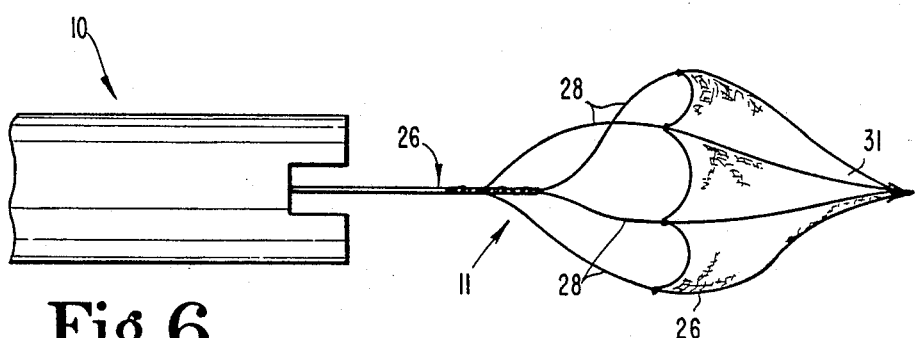
FIG. 6 is an enlarged fragmentary elevation view of the distal end of the catheter of the present invention and showing the parachute basket in its deployed position.
Figure 7:
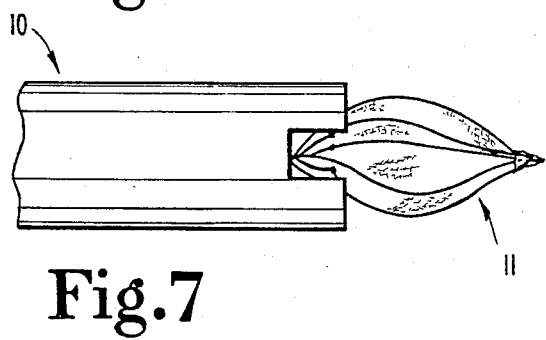
FIG. 7 is an enlarged fragmentary elevation view of the distal end of the catheter of the present invention and showing the parachute basket in a stowed position.
Figure 8:
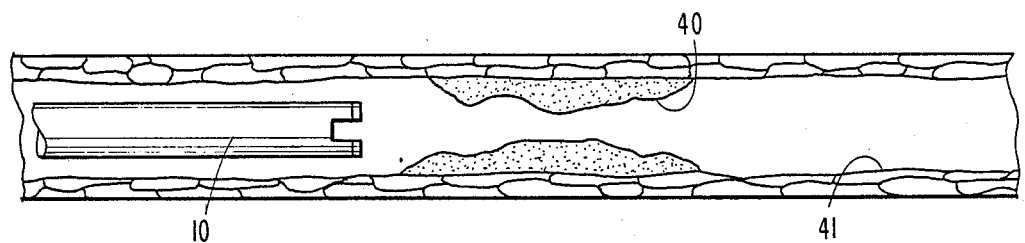
FIGS. 8-11 depict successive steps in practicing the method of the present invention to remove atheroma from a blood vessel.

Referring to FIGS. 6 and 7, parachute basket 11 includes a basket portion 25 and a control wire 26 which extends proximally from the basket portion within lumen 16 of catheter 10. Control wire 26 is connected to a suitable external manipulating means, which may be example be a three ring handle. Basket portion 25 includes a plurality of resilient and flexible spring wires 28 connected at their respective ends by suitable means, such as a solder or weld. Each of the spring wires 28 have a preformed helical shape along their length. This permits the spring wires 28 to spring outwardly apart as the control wire 26 is advanced relative to catheter 10 by manipulation of the handle at the operator end in order to deploy the parachute basket as shown in FIG. 6. When not deployed, basket portion 25 may be stowed by retracting the spring wires to a position partially within the distal open end 23 of catheter 10. Alternatively, basket portion 25 may be stowed within a sheath catheter 29 (FIG. 10) sized to be slidably received within catheter 10. At the distal portion of parachute basket 11, a web 31 extends between the spring wires 28. The web 31 is formed of a thin porous fabric, compatible for insertion within the body, which is so constructed to allow the passage of blood and its constituents, but yet prevent passage of emboli, atheroma or other undesirable objects therethrough.

Control wire 26 is made of a metal having good flexibility characteristics such as stainless steel. The control wires 26 has a length which is sufficiently longer than catheter 10 to allow the basket portion 25 to be extended outside the distal open end of catheter 10 for positioning downstream of the target site with catheter 10 positioned upstream of the target site.

Drilling device 13 includes a flexible, elongate tubular wire 35 and a slightly conically tapered drill head 36 fixedly secured to tubular wire 35 at the distal end. Tubular wire 35 is rotatably coupled at the proximal end with the output shaft of a second air actuated drive motor 15b by a suitable quick connect disconnect coupling. Tubular wire 35 is flexible along its length and is made from a material exhibiting good torque transmission characteristics. Tubular wire 35 may for example be made of stainless steel and have a construction similar to conventional catheter wire guides. Both wire 35 and drill head 36 define an inner lumen along their length which is sized to allow the drilling device to be advanced over the control wire 26 of parachute basket 11.

Referring to FIGS. 8-11, the operation of the apparatus of the invention in removing a target object, such as a stenosis in a blood vessel, may be described as follows. Access inside the blood vessel is initially gained by a suitable entry method such as a surgical cutdown or the Seldinger technique. Catheter 10 may then be inserted into the blood vessel and maneuvered to the target site by advancement transluminally within the blood vessel over a standard guide wire (not shown). Once the catheter 10 is maneuvered to the target site (FIG. 8) the guide wire is removed, and the spiral wound coil 12 is inserted inside the catheter.

Figure 9:
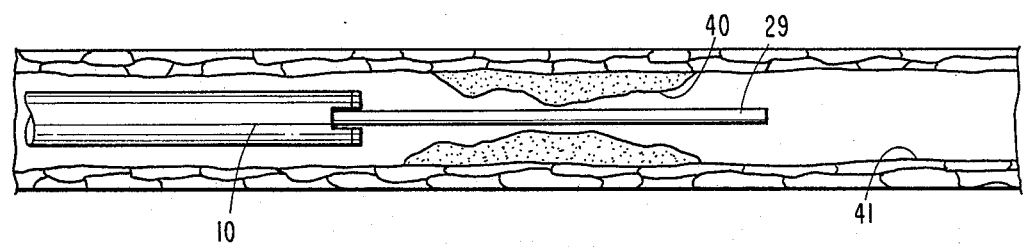
Figure 10:
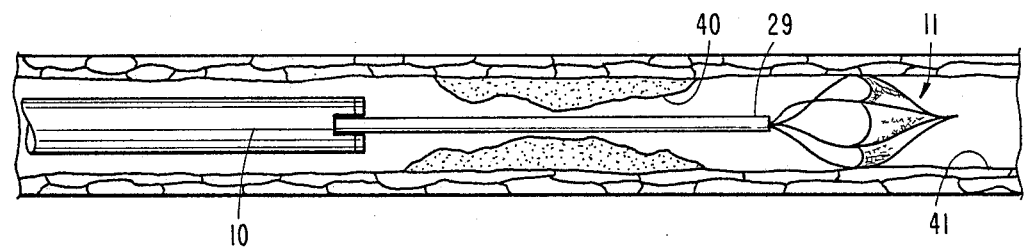
Figure 11:
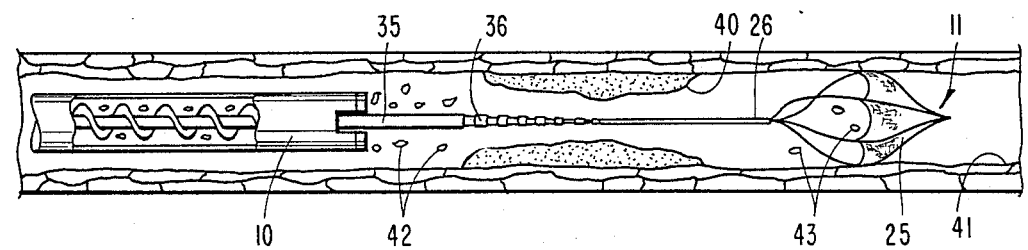

FIGS. 9-11 depict successive steps in the operation of spiral wound coil 12, parachute basket 11 and drilling device 13. First, parachute basket 11 is advanced downstream through the stenosis 40 inside catheter sheath 29 with the distal open end of catheter 10 maintained in a position slightly upstream of the stenosis 40 (FIG. 9). Once the catheter sheath 29 with parachute basket 11 inside has crossed the stenosis 40, the parachute basket 11 is deployed by extending it outside the distal open end of catheter sheath 29. Once the parachute basket is deployed downstream of the stenoisis 40, the catheter sheath 29 may be removed from the body (FIG. 10).

Next, the atheroma forming the stenosis 40 is fragmented by advancing the drilling device 13 over the control wire 26 of parachute basket 11 into contact with the stenosis and activating the motor 15b driving drilling device 13 (FIG. 11). As the head 36 of the drilling device 13 rotates at high speed in the area of the stenosis, atheroma fragments will be generated. At the same time as the drilling operation is commenced, drive means 15 is activated to operate spiral wound coil 12 and aspiration of lumen 16 is initiated by employing suction device 14. Atheroma fragments 42 will be urged upstream into lumen 16 of catheter 10 by suction provided by suction device 14. As the atheroma fragments are urged inside lumen 16 through slots 24 and distal open end 23, rotation of the cutting tip 17 of spiral wound coil 12 will further reduce the size of the fragments so as to reduce the possibility of lumen 16 becoming clogged. Rotation of the sprial wound coil 12 inside lumen 16 also facilitates transportation of the fragments outside the body by screw movement. Fragments 43 which are not aspirated inside lumen 16 will flow downstream and be captured inside parachute basket 11. Once the drilling operation is completed, the parachute basket 11 is retracted to a stowed position into catheter 10 and removed from the body along with catheter 10.

Figure 5:
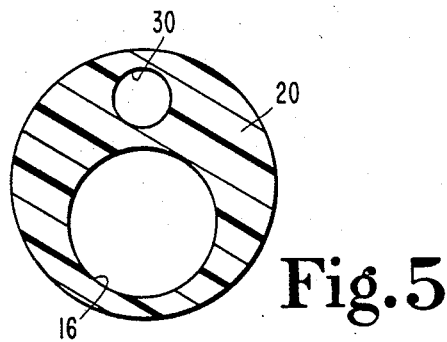
FIG. 5 is a cross section view of an alternative embodiment of the catheter of the present invention.

If saline injection is desired to soften the atheroma or clot prior to commencing the drilling operation, a catheter 20 having a bilumen construction, shown in FIG. 5, is employed instead of the single lumen catheter 10. Saline injection is provided in catheter 20 through lumen 30.

It should be noted that there could exist some risk of damage to the intimal wall 41 of the blood vessel by operation of drilling device 31. This risk, however, is greatly minimized by the fact that the distal end of drilling device 13 cannot be advanced into the blood vessel intimal wall 41 since it is received over control wire 26 of parachute basket 11. Advancement of the drilling device 13 over control wire 26 thus tends to keep the drilling head 36 medially positioned within the blood vessel. Also, since the cutting tip 17 of coil 12 is entirely received within catheter 10 and prevented from extending outside catheter 10 by grommet 18, the risk of puncturing or otherwise damaging the blood vessel wall 41 from operation of cutting tip 17 is also greatly reduced.

If for any reason the spiral wound coil 12 becomes clogged by fragments, the quick connect disconnect coupling to drive means 15 allows quick exchange of coil 12 with a new coil. It may also be appreciated that the use of air actuated motors to drive coil 12 and drilling device 13 eliminates any electrical hazard which could be caused by the use of electrically powered drive means.

Figure 12:
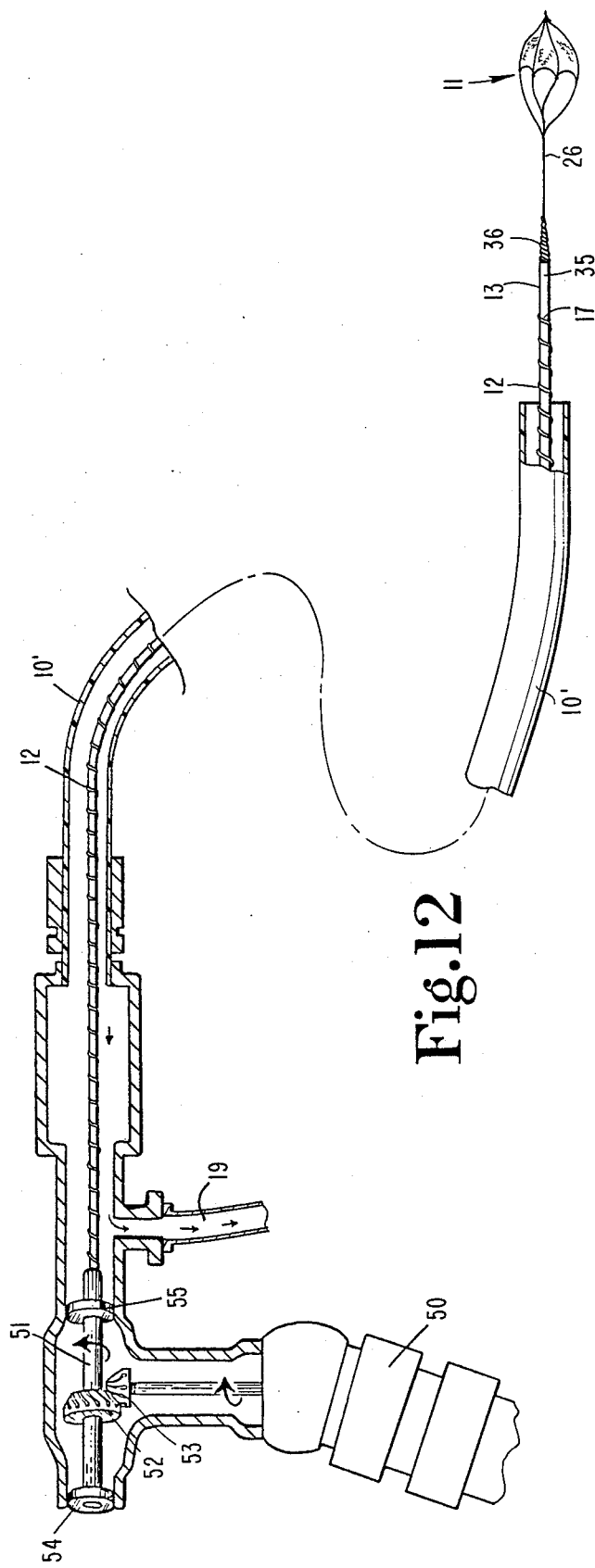
FIG. 12 is a fragmentary elevation view, with certain sections broken away, depicting an alternative embodiment of the apparatus of the invention employing a common drive means for driving the spiral coil and drilling device.

While FIG. 1 shows the spiral would coil 12 and drilling device 13 being driven by separate motors 15a and 15b, in an alternative preferred embodiment the apparatus of the invention may have only one motor 50 driving both coil 12 and drilling device 13. Such an embodiment is depicted in FIG. 12, which shows the internal drive mechanism connecting the motor 50, which may be of a similar type as motors 15a and 15b in FIG. 1, to the coil 12 and drilling device 13. In this embodiment, coil 12 and drilling device 13 are attached proximally to a common shaft 51 linked by a suitable quick release coupling to a gear reduction mechanism comprising gears 52 and 53. Motor 50 and gears 52 and 53 are isolated from coil 12, drilling tool 13 and sealed from leakage by a pair of resilient flexible O-rings 54 and 55. Catheter 10' is different from catheter 10 of the previous preferred embodiment in that no grommet is provided at the distal end, which is of a simple tubular construction. Thus, the cutting tip of spiral wound coil 12 is allowed to extend outside the distal end of catheter 10' as the drilling device 13 is advanced into contact with the target. The possibility of the cutting tip 17 penetrating the vessel wall is prevented due to the fact that the coil 12 is received over the control wire 35 of drilling device 13, which is in turn received over wire 26 of basket 11.

It should be appreciated that while removal of atheroma in conjunction with the canalization of a stenosed blood vessel is depicted in the drawings, the apparatus and procedure may also be readily adapted for use in removing blood clots and other undesirable objects from blood vessels and other body passageways or cavities. For example, if the target object is a blood clot, fragmentation and removal of the target object can be accomplished in a manner similar to that already described but without drilling device 13 and often also without employing parachute basket 11. The two lumen catheter 20 embodiment is preferred for clot removal because it permits saline infusion during the procedure to soften the clot prior to fragmentation and to facilitate transport inside central lumen 16. When distal migration of the blood clot is a possibility, the parachute basket 11 is inserted through the catheter lumen 16 and employed in a similar manner as described when canalizing a stenosis. The drilling device 13 and the parachute basket 11 are always inserted within the catheter lumen 16 for the removal of atheroma and stones. When the target object is a blood cot, the catheter 10 should be advanced into the clot before removing the guide wire, since blood loss can occur during the insertion of basket 11 and coil 12 within catheter 10.

As a further example, either embodiment of the apparatus of the invention may be used, without the parachute basket and with the drilling device having a macerating tip, simultaneously in conjunction with conventional shock wave lithotripsy (ESWL) techniques for removal of kidney stones to further fragment and transport stones from the urinary tract. In this use, the catheter will have the two lumen configuration shown in FIG. 5, the second lumen being used to infuse a relatively large volume of fluid to prevent collapse of the system (renal pelvis, ureter, bladder, etc.) as the spiral and suction is transporting the stones. Use of the apparatus in this manner would obviate the need for a percutaneous nephrostomy to drain the kidney after the procedure. It will also expedite the procedure, since by removing the debris as the procedure is performed, the shock wave energy will be more efficiently used, and the number of bombardments which can cause damage to the kidney will be reduced.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for removing a target object from a body passageway by fragmenting the target object into a plurality of fragments and transporting the fragments outside the body, said apparatus comprising:
   a catheter having proximal and distal open ends and having at least one lumen therethrough;
   a spiral wound coil having proximal and distal ends and rotatably disposed within said lumen in said catheter, said spiral wound coil being resilient and flexible along its length;
   a cutting tip means formed at the distal end of said coil for engaging and fragmenting the target object so that the resulting fragments can be transported within said catheter to outside the body;
   means associated with said catheter for retaining said cutting tip within said catheter and proximate the distal open end of said catheter, thereby preventing said cutting tip from extending out beyond the distal open end of said catheter;
   an elongated control wire slidably disposed within a lumen of said catheter;
   a parachute basket means fixed to the distal end of said control wire and sized and shaped to be advanced through the lumen in a stowed position, said parachute basket means when deployed being capable of permitting the flow of fluid but preventing passage of fragements from the target object;
   means for advancing the control wire and said parachute basket means beyond the distal end of said catheter to permit said parachute basket means to open to a deployed position within the body passageway; and
   a first drive means for rotatably driving said spiral wound coil within said lumen in order to create a flow which pulls the target body through the distal open end of said catheter toward said cutting tip and transports fragmented portions of the target body through said lumen by a screw movement of said coil.

2. The apparatus of claim 1 wherein said retaining means includes a grommet attached to said catheter, positioned adjacent the distal open end of said catheter, and sized to prevent said coil and cutting tip means from extending through said distal open end.

3. The apparatus of claim 2 wherein said cutting tip is maintained proximate the distal end of said catheter by the spring bias of said spiral wound coil against said grommet.

4. The apparatus of claim 2 further comprising means for urging the distal end of said coil against said grommet.

5. The apparatus of claim 1 further including a plurality of angularly spaced apart openings cut in the sides of said catheter and aligned with said cutting tip means.

6. The apparatus of claims 1 wherein said parachute basket includes a plurality of loosely helical formed spring wires connected at their respective ends and a thin porous web attached to and extending between said spring wires.

7. An apparatus for removing a target object from a body passageway or cavity by fragmenting the target object into a plurality of fragments and transporting the fragments outside the body, said apparatus comprising:
   a catheter having proximal and distal open ends and having at least one lumen therethrough;
   a spiral wound coil having proximal and distal ends and rotatably disposed within said lumen in said catheter, said spiral wound coil being resilient and flexible along its length;
   cutting tip means formed at the distal end of said coil for engaging and fragmenting the target object;
   a drilling tool means extending through said lumen in said catheter for engaging and fragmenting the target object so that the resulting fragments can be transported within said catheter to outside the body, said drill tool means having proximal and distal ends and having a bore along its length and a drilling head at its distal end;
   a control wire extending through the bore of said drilling tool and through the lumen of said catheter and beyond the distal end of said catheter for guiding the drilling tool and preventing the drilling head from rupturing the body passageway;
   a first drive means for rotatably driving said spiral wound coil within said lumen in order to create a flow which transports the fragmented portions of the target body through said lumen by a screw movement of said coil; and
   a second drive means attached to said drilling tool for rotatably driving said drilling tool.

8. The apparatus of claim 7 further comprising:
   a parachute basket means connected to the distal end of said control wire and sized and shaped to be advanced through said lumen in a stowed position, said parachute basket means when deployed being capable of permitting the flow of fluid but preventing passage of fragments from the target object; and
   means for advancing the parachute basket means beyond the distal end of said catheter and beyond the distal end of said drill tool means and then permitting said parachute basket means to open to a deployed position within the body passageway.

9. The apparatus of claim 8 further comprising a sheath catheter means slidably disposed within said catheter and slidably disposed on said control line for covering said parachute basket and holding it in a stowed position until it is advanced past the target object.

10. The apparatus of claim 7 wherein said coil is slidably disposed on said drill tool means.

11. The apparatus of claims 1 or 7 further comprising an aspirating means for providing aspiration with said lumen or said catheter to thereby facilitate transportation of the target object with said lumen.

12. The apparatus of claim 11 wherein said aspirating means is a syringe.

13. The apparatus of claim 7 wherein said cutting tip is spiral shaped.

14. The apparatus of claims 1 or 7 wherein said catheter includes a second lumen for permitting saline injection therethrough.

15. An apparatus for removing a target object from a body passageway or cavity by fragmenting the target object into a plurality of fragments and transporting the fragments outside the body, said apparatus comprising:
   a catheter having proximal and distal open ends and having at least one lumen therethrough;
   a spiral wound coil having proximal and distal ends and rotatably disposed within said lumen in said catheter, said spiral wound coil being resilient and flexible along its length;

a drilling tool means extending through said lumen in said catheter for engaging and fragmenting the target object so that the resulting fragments can be transported within said catheter to outside the body, said drill tool means having proximal and distal ends and having a bore along its length and a drilling head at its distal end;

a control wire extending through the bore of said drilling tool and through the lumen of said catheter and beyond the distal end of said catheter for guiding the drilling tool and preventing the drilling head from rupturing the body passageway;

a parachute basket means, including a plurality of loosely helical formed spring wires connected at their respective ends and a thin porous web attached to and extending between said spring wires, connected to the distal end of said control wire and sized and shaped to be advanced through said lumen in a stowed position, said paracute basket means when deployed being capable of permitting the flow of fluid but preventing passage of fragments from the target object;

means for advancing the parachute basket means beyond the distal end of said catheter and beyond the distal end of said drill tool means and then permitting said parachute basket means to open to a deployed position within the body passageway;

a first drive means for rotatably driving said spiral wound coil within said lumen in order to create a flow which transports the fragmented portions of the target body through said lumen by a screw movement of said coil; and a second drive means attached to said drilling tool for rotatably driving said drilling tool.

* * * * *